(12) United States Patent
Dunn et al.

(10) Patent No.: US 12,109,006 B2
(45) Date of Patent: Oct. 8, 2024

(54) OPTICAL SPECKLE RECEIVER

(71) Applicant: ROCKLEY PHOTONICS LIMITED, Altrincham (GB)

(72) Inventors: Cody Dunn, Costa Mesa, CA (US); Kate Leeann Bechtel, Pleasant Hill, CA (US)

(73) Assignee: Rockley Photonics Limited, Altrincham (GB)

( * ) Notice: Subject to any disclaimer, the term of this patent is extended or adjusted under 35 U.S.C. 154(b) by 281 days.

(21) Appl. No.: 17/703,920

(22) Filed: Mar. 24, 2022

(65) Prior Publication Data

US 2023/0085179 A1    Mar. 16, 2023

Related U.S. Application Data

(60) Provisional application No. 63/243,021, filed on Sep. 10, 2021.

(51) Int. Cl.
*A61B 5/00*        (2006.01)
*G01B 9/02055*    (2022.01)
*G02B 3/00*        (2006.01)

(52) U.S. Cl.
CPC ........ *A61B 5/0028* (2013.01); *G01B 9/02082* (2013.01); *G02B 3/0006* (2013.01)

(58) Field of Classification Search
CPC ............. A61B 5/0028; G01B 9/02082; G02B 3/0006; G02B 27/46; G02B 27/48
See application file for complete search history.

(56) References Cited

U.S. PATENT DOCUMENTS

| | | | |
|---|---|---|---|
| 4,674,011 A | 6/1987 | Patton et al. | |
| 5,497,769 A | 3/1996 | Gratton et al. | |
| 5,532,860 A * | 7/1996 | Hershey | G02B 27/48 356/508 |
| 6,154,259 A | 11/2000 | Hargis et al. | |
| 6,243,601 B1 | 6/2001 | Wist | |
| 6,256,016 B1 | 7/2001 | Piot et al. | |
| 7,202,466 B2 * | 4/2007 | Babayoff | G02B 27/0933 359/368 |
| 7,474,407 B2 | 1/2009 | Gutin | |
| 9,848,787 B2 | 12/2017 | White et al. | |

(Continued)

FOREIGN PATENT DOCUMENTS

| | | | | |
|---|---|---|---|---|
| CA | 2861089 C | * | 1/2021 | ........... A61B 5/0035 |
| CN | 112639582 A | * | 4/2021 | ........... A61B 3/0025 |
| CN | 114466549 A | * | 5/2022 | ........... A61B 5/0059 |

OTHER PUBLICATIONS

U.S. Advisory Action for U.S. Appl. No. 17/822,419, dated Oct. 10, 2023, 6 pages.

(Continued)

*Primary Examiner* — Mohamed K Amara
(74) *Attorney, Agent, or Firm* — Lewis Roca Rothgerber Christie LLP

(57) ABSTRACT

An optical speckle receiver for receiving a speckle signal from a sample, the optical speckle receiver comprising an optical detector and an aperture and/or lens array. The aperture and array respectively comprise a plurality of apertures or lenses and is located between the sample and the optical detector such that the received speckle pattern is obtained from multiple discrete sample locations.

20 Claims, 15 Drawing Sheets

(56) References Cited

U.S. PATENT DOCUMENTS

| | | |
|---|---|---|
| 9,851,298 B1 | 12/2017 | Isikman et al. |
| 10,813,597 B2 | 10/2020 | Rice et al. |
| 10,895,525 B2 | 1/2021 | Swanson |
| 2002/0195496 A1 | 12/2002 | Tsikos et al. |
| 2003/0052169 A1 | 3/2003 | Tsikos et al. |
| 2003/0137669 A1 | 7/2003 | Rollins et al. |
| 2006/0132790 A1 | 6/2006 | Gutin |
| 2007/0051601 A1 | 3/2007 | Wang et al. |
| 2007/0057182 A1 | 3/2007 | Feuerbaum |
| 2007/0093702 A1 | 4/2007 | Yu et al. |
| 2008/0154126 A1 | 6/2008 | Culver et al. |
| 2009/0177094 A1 | 7/2009 | Brown et al. |
| 2009/0284748 A1 | 11/2009 | Melman et al. |
| 2010/0004741 A1 | 1/2010 | Gupta et al. |
| 2010/0046234 A1 | 2/2010 | Abu-Ageel |
| 2010/0226646 A1 | 9/2010 | Chan et al. |
| 2012/0232402 A1 | 9/2012 | MacFarlane et al. |
| 2013/0204112 A1 | 8/2013 | White et al. |
| 2013/0278631 A1 | 10/2013 | Border et al. |
| 2014/0118695 A1 | 5/2014 | Shimada et al. |
| 2014/0120319 A1 | 5/2014 | Joseph |
| 2014/0313524 A1* | 10/2014 | Banyay ................ A61C 19/04 433/29 |
| 2016/0183882 A1* | 6/2016 | Henley ............. G02B 23/2469 600/103 |
| 2016/0195473 A1 | 7/2016 | Fujiwara et al. |
| 2016/0242647 A1 | 8/2016 | Ishii et al. |
| 2016/0360966 A1 | 12/2016 | Ishii et al. |
| 2017/0105618 A1 | 4/2017 | Schmoll et al. |
| 2017/0164878 A1 | 6/2017 | Connor |
| 2018/0020962 A1 | 1/2018 | Yu et al. |
| 2018/0202927 A1 | 7/2018 | Isikman et al. |
| 2018/0228363 A1 | 8/2018 | Frisken et al. |
| 2019/0041736 A1 | 2/2019 | Grunnet-Jepsen et al. |
| 2019/0053721 A1 | 2/2019 | Boas et al. |
| 2019/0094564 A1 | 3/2019 | Rivera et al. |
| 2019/0369650 A1 | 12/2019 | Swanson et al. |
| 2020/0011995 A1 | 1/2020 | Send et al. |
| 2020/0143534 A1 | 5/2020 | Wright et al. |
| 2020/0158548 A1 | 5/2020 | Rice et al. |
| 2020/0237272 A1 | 7/2020 | Lin et al. |
| 2020/0249492 A1 | 8/2020 | Maes |
| 2021/0161408 A1 | 6/2021 | Wakita |
| 2021/0321887 A1 | 10/2021 | Fukazawa et al. |
| 2021/0338083 A1* | 11/2021 | Sie ..................... A61B 5/6803 |
| 2021/0405518 A1 | 12/2021 | Lablans |
| 2022/0018762 A1 | 1/2022 | Ekin et al. |
| 2022/0061644 A1 | 3/2022 | Fontaine et al. |
| 2022/0104822 A1 | 4/2022 | Shelton, IV et al. |
| 2022/0196557 A1* | 6/2022 | Zheng .................. G01J 3/0278 |
| 2023/0048766 A1 | 2/2023 | Frey |
| 2023/0064006 A1 | 3/2023 | Kim et al. |
| 2023/0164444 A1 | 5/2023 | Yang |
| 2023/0296510 A1 | 9/2023 | Xu |
| 2024/0032790 A1 | 2/2024 | Patel et al. |

OTHER PUBLICATIONS

U.S. Office Action for U.S. Appl. No. 17/822,419, dated Nov. 3, 2023, 18 pages.

International Search Report and Written Opinion of the International Searching Authority, mailed Jan. 2, 2023, corresponding to PCT/EP2022/074876, 13 pages.

U.S. Office Action from U.S. Appl. No. 17/822,419, dated Mar. 10, 2023, 17 pages.

Zalevsky, Z. et al., "Novel Approaches for Near and Far Field Super Resolved Imaging", 22nd Congress of the International Commision for Optics: Light for the Development of the World, Proc. of SPIE, Sep. 15, 2011, pp. 80116M-1 through 80116M-11, vol. 8011, No. 1, SPIE.

U.S. Office Action from U.S. Appl. No. 17/822,419, dated Jul. 20, 2023, 21 pages.

Bi, R. et al., "Fast pulsatile blood flow measurement in deep tissue through a multimode detection fiber", Journal of Biomedical Optics, May 13, 2020, pp. 055003-1 through 055003-10, vol. 25(5), SPIE.

Goodman, J. W., "Some fundamental properties of speckle", Journal of the Optical Society of America, Nov. 1976, pp. 1145-1150, vol. 66, No. 11, Optical Society of America.

Robinson, M. B. et al., "Interferometric diffuse correlation spectroscopy improves measurements at long source-detector separation and low photon count rate", Journal of Biomedical Optics, Sep. 30, 2020, pp. 097004-1 through 097004-12, vol. 25(9), SPIE.

Sdobnov, A. Y. et al. "Speckle dynamics under ergodicity breaking", Journal of Physics D: Applied Physics, Mar. 26, 2018, pp. 1-21, vol. 51, No. 15, IOP Publishing Ltd.

Website: "FlowMet Peripheral Blood Flow Monitoring System", updated Oct. 2022, printed Dec. 7, 2022, 7 pages, https://www.medtronic.com/us-en/healthcare-professionals/products/cardiovascular/intraprocedural-monitoring/flowmet.html.

Website: "0.07mm Dia., TO-46 Package, InGaAs Photodiode", 2022, printed Dec. 7, 2022, 1 page, Edmund Optics Inc., https://www.edmundoptics.com/p/ingaas-detector-70mum-dia-to-46/12571/.

Xu, J. et al., "Interferometric speckle visibility spectroscopy (ISVS) for human cerebral blood flow monitoring", APL Photonics, Dec. 4, 2020, pp. 126102-1 through 126102-10, vol. 5. AIP Publishing.

U.S. Appl. No. 17/822,419, filed Aug. 25, 2022.

U.S. Office Action for U.S. Appl. No. 17/822,419, dated Feb. 20, 2024, 12 pages.

U.S. Advisory Action for U.S. Appl. No. 17/822,419, dated May 2, 2024, 5 pages.

* cited by examiner

Aperture Array
EN FACE VIEW

Lens Array
EN FACE VIEW

OPTICAL SPECKLE RECEIVER

RELATED APPLICATIONS

The present application claims priority to, and the benefit of, U.S. 63/243,021 filed 10 Sep. 2021, the contents of which are incorporated herein by reference in their entirety.

FIELD OF THE INVENTION

The present invention relates to an optical speckle receiver, comprising an optical detector and an aperture array or a lens array, an optical transceiver, and a wearable device.

BACKGROUND

In various clinical or home health care settings, obtaining optical data (for example spectrophotometric data) from tissue of a subject may be advantageous, e.g., to sense levels of chemical compounds (for example glucose) in the tissue, to measure other characteristics (for example temperature) of the tissue, or to distinguish different kinds of tissue (for example healthy from diseased tissue).

In some cases, the spectrophotometric data includes speckle data as obtained by a speckleplethysmography device. Speckle fluctuations due to the interaction of coherent light with dynamic scatterers (for example red blood cells) can be quantified to monitor various physiological parameters (for example blood flow). Speckle size-to-sensor pixel size matching is typically achieved via single mode fiber for photodiodes or an aperture or multimode fiber with or without a lens system for image sensors.

However, such systems are unsuited for integration into wearable devices as either the amount of light collected is too low for optimal use or the distance between the tissue and the optical detector is too large. Wearable spectrophotometric devices broaden the applications of spectrophotometry and improve compliance in monitoring. There is a desire then to facilitate the integration of optical receivers suitable for receiving speckle signals with miniaturized, wearable devices.

SUMMARY

Accordingly, in some embodiments, the present invention provides an optical speckle receiver, which may be referred to as an optical receiver, for receiving a speckle signal from a sample or surface, the optical speckle receiver comprising an optical detector and an aperture array and/or a lens array, wherein, the aperture array and/or lens array respectively comprise a plurality of apertures or lenses and is located between, or in-between, the surface or sample and the optical detector such that the received speckle pattern is obtained from multiple discrete sample locations.

Receiving a speckle pattern from multiple sample locations may be counterintuitive as adding M uncorrelated speckle patterns on an intensity basis reduces speckle contrast by 1/sqrt(M), which is undesirable. However, if the speckle patterns are generated by the same coherent source and are physically separated by a distance larger than the correlation distance such that the patterns generated are independent, then the speckle patterns add on a complex amplitude basis, not intensity, and the speckle contrast is not reduced. [J. W. Goodman, "Some fundamental properties of speckle" J. Opt. Soc. Am. 66(11):1145-1150, 1976].

By providing such an aperture array or lens array, sampling of a speckle pattern can be undertaken by a compact sensor with a reduced height from the sample or surface whilst maintaining an acceptable signal-to-noise ratio. Further, the aperture array or lens array can ensure that only light which has more deeply interacted with the sample, and not just the surface, is detected.

Optional features of the invention will now be set out. These are applicable singly or in any combination with any aspect of the invention.

In some, but not all, examples, the plurality of apertures or lenses includes an element of ordering or structure but in yet other examples the apertures or lenses in the respective arrays may be unordered or unstructured. By aperture, it may be meant an inlet or opening for light in the otherwise opaque plate. By lens, it may be meant an optical element with focal length designed to produce optimal speckle size as compared to sensor pixel size based on the distance between the optical element(s) and the sensor.

The aperture array or lens array being located between, or in-between, the surface of the sample and the optical detector may be such that the speckle pattern at the surface can be viewed by the optical detector through each of the apertures.

The sample or surface may be tissue. By tissue, it is meant biological tissue such as human skin. In some examples, the surface may be the skin of a patient who is to have a biomarker value derived from the speckle signal. The skin may be skin on or around the wrist, specifically a dorsal portion of the wrist or ulnar or radial portion of the wrist.

The aperture array may be a plate, and the plate may define or include within it a plurality of holes, each hole corresponding to an aperture of the aperture array. The holes may have a uniform cross-section as they extend through the plate, or may have a cross-section which varies as a function of depth.

The aperture array may include an array of single mode or multi-mode fibers, each single mode or multi-mode fiber corresponding to an aperture of the aperture array. That is, each aperture in the aperture array may be provided with an end of an optical fiber. The aperture array may be a plate in which each of the optical fibers are integrally formed.

The optical detector may be a photodiode or a pixel array such as an image sensor. The optical detector may include a plurality of photodiodes or may, in some examples, be a charge-coupled device.

The relationship between aperture diameter (D) of apertures in the aperture array and the distance (Z) between the tissue or surface and the optical detector is governed by $S = \lambda Z/D$ where $S$ is the speckle diameter and $\lambda$ is the wavelength of light; and wherein the parameters are chosen such that Z has a value of less than 5 cm, less than 2 cm, less than 1 cm, less than 0.5 cm, or less than 0.1 cm. By wavelength of light, it may be meant the wavelength of the light which is forming the speckle. All of the apertures in the aperture array may have a same cross-sectional shape, for example a circle, square, rectangle, or triangle. In other examples, some of the apertures in the aperture array may have different cross-sections to other apertures in the aperture array. The apertures in the aperture array may be identically dimensioned (e.g. having a same diameter where circular), or some apertures in the aperture array may have dimensions which are different to other apertures in the aperture array.

The relationship between lens $f_\#$, magnification (M) and the distance (Z) between the tissue or surface and the optical detector is governed by $S \approx 1.2(1+M)\lambda f_\#$ where $f_\#$ is the ratio between the lens focal distance and the effective aperture of the lens. The parameters may be chosen such that Z has a value of less than 5 cm, less than 2 cm, less than 1 cm, less than 0.5 cm, or less than 0.1 cm. By wavelength of light, it may be meant the wavelength of the light which forms the speckle. The lenses in the lens array may be spherical, aspherical, cylindrical, or may be customized to any particular shape that serves the purpose of projecting light onto the detector with desired speckle size.

In a second aspect, embodiments of the invention provide an optical transceiver comprising the optical speckle receiver of the first aspect and a coherent light source. The optical transceiver may have any one, or any combination insofar as they are compatible, of the optional features as set out with reference to the first aspect.

The coherent light source may operate at one or more ultraviolet to far infrared (IR) wavelengths. Herein, the wavelength range may be understood as being between 280 nm and 1 mm. In some examples the coherent light source may operate at 1300 nm. The coherent light source may be a laser.

The coherent light source may include a coherent light source operating at one or more visible wavelengths.

The optical transmitter and optical speckle receiver together make an optical transceiver which may be arranged in a reflection mode such that light from the coherent light source interacts with the tissue and produces speckle at the tissue which is captured by the detector. The aperture array and/or lens array, placed between the tissue and detector, receives speckle from the tissue (both the surface and tissue beneath the surface) and passes this light through its apertures or lenses to the optical detector. The aperture array and/or lens array also helps manipulate the size of the speckles received by the detector. The relationship between the aperture array or lens array, the tissue, and the light source can be designed to prevent specular reflectance (that is, to ensure that light interacts with dynamic scatterers in the tissue).

The transceiver may be arranged in a transmission mode, such that light from the coherent light source produces speckle through the tissue, the aperture positioned to receive light transmitted through the tissue, through its apertures or lenses, to the optical detector.

In a third aspect, embodiments of the invention provide a wearable device including the optical receiver of the first aspect or the optical transceiver of the second aspect. The optical receiver may have any one, or insofar as they are compatible, any combination of the optional features as set out with reference to the first aspect. The optical transceiver may have any one, or insofar as they are compatible, any combination of the optional features as set out with reference to the second aspect.

The aperture plate and/or lens array may form a portion of an outer casing of the wearable device.

The lens array and aperture array may operate independently or together in the same device.

In a fourth aspect, embodiments of the invention provide an aperture array or lens array respectively comprising a plurality of apertures or lenses, the aperture array or lens array configured to be located in-between tissue and a photodiode or optical detector such that speckle patterns at the tissue can be acquired by the optical detector through the plurality of apertures or lenses (that is, combined on the photodiode or optical detector).

The invention includes the combination of the aspects and preferred features described except where such a combination is clearly impermissible or expressly avoided.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES

Figure 1A:
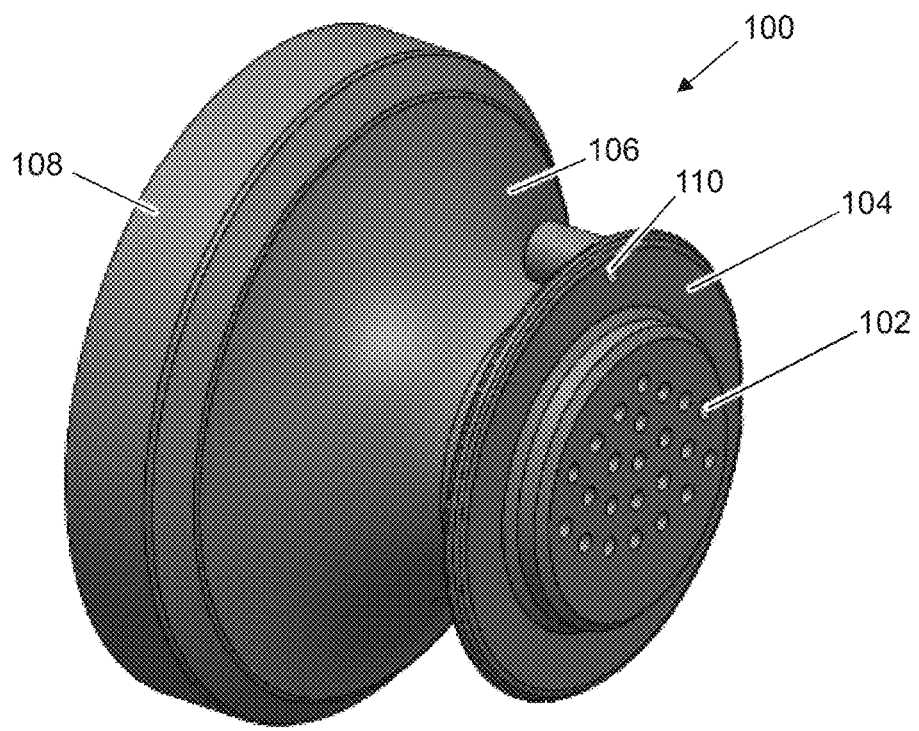
FIGS. 1A and 1B show an aperture array from a perspective and front-on view respectively.
Figure 1B:
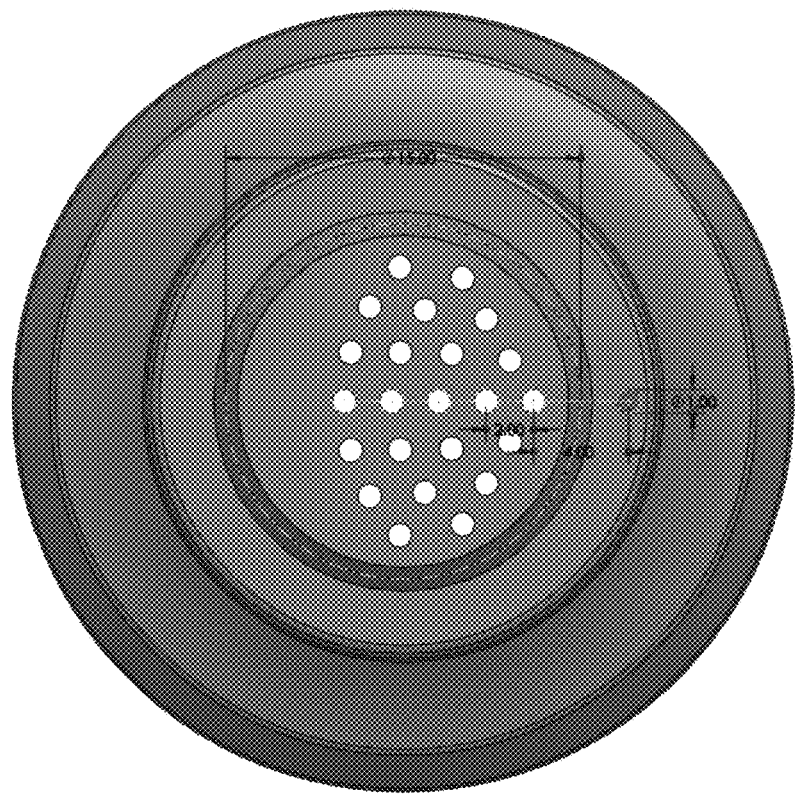

Aspects and embodiments of the present invention will now be discussed with reference to the accompanying figures. Further aspects and embodiments will be apparent to those skilled in the art. All documents mentioned in this text are incorporated herein by reference FIGS. 1A and 1B show an aperture array 100 from a perspective and front-on view respectively. The aperture array in this example includes a plurality of apertures 102. In this example the apertures are located on a flange or protrusion 104 spaced from a base 106 via a neck 108. As can be seen in FIG. 1B, the apertures have an outer diameter of 1 mm. The flange or protrusion has a diameter of around 15 mm. The apertures are arranged in an array, in this example being formed of 23 apertures. Apertures within a row are spaced by 2 mm (centre to centre). An input aperture 110 is provided, offset both vertically and horizontally from the aperture array, and through which a sample is illuminated.

Figure 2A:
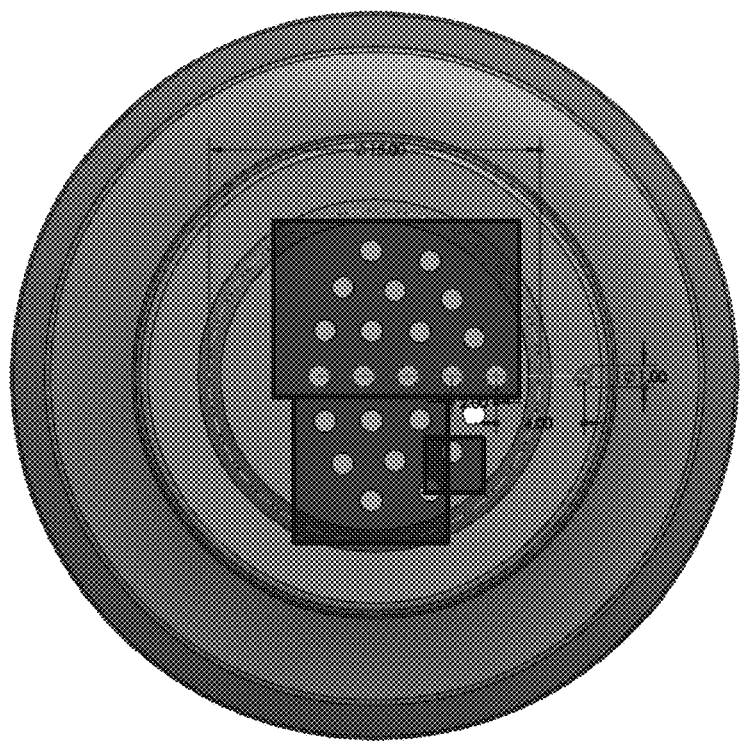
FIGS. 2A, 2B, and 2C show the aperture array in various configurations as used during testing.
Figure 2B:
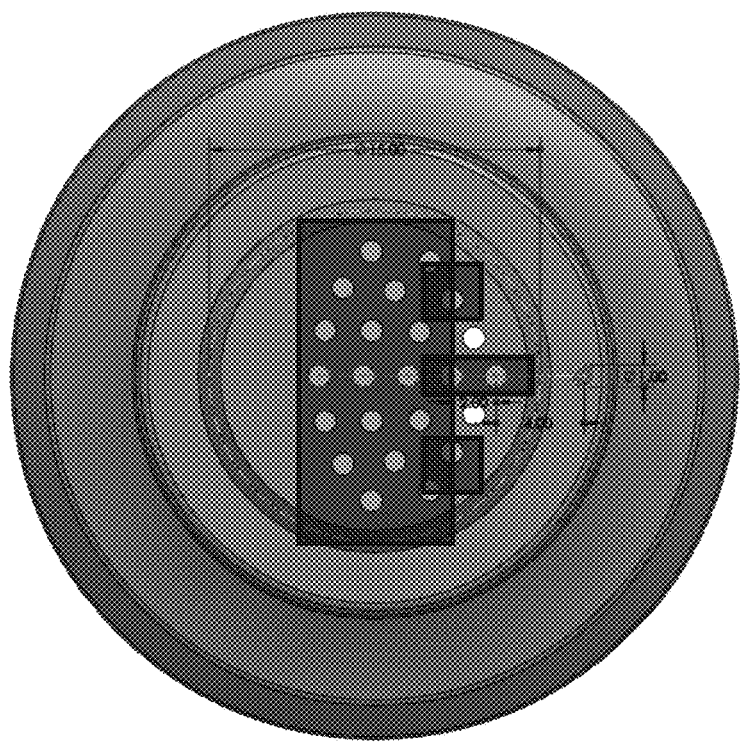
Figure 2C:
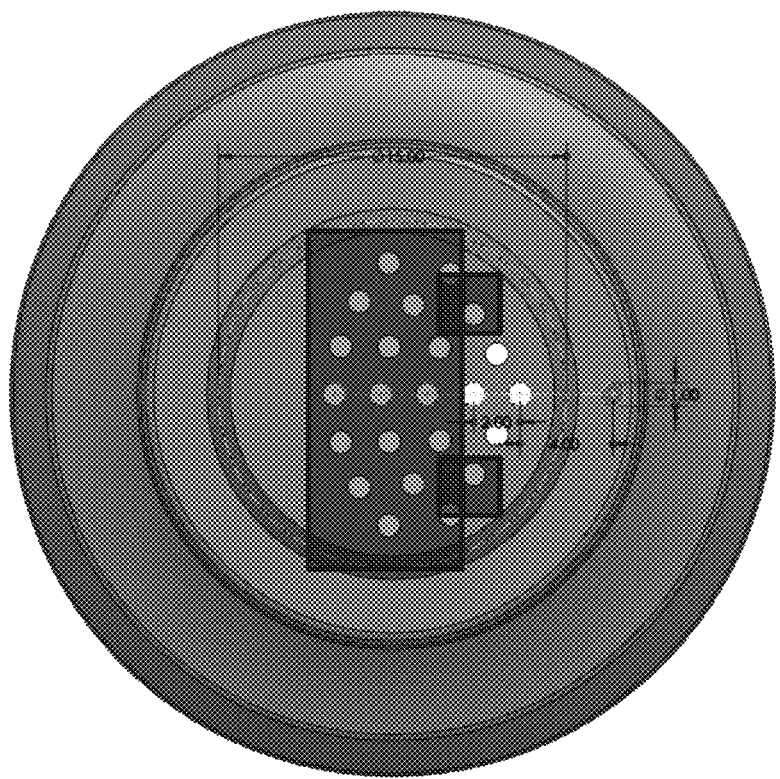

FIGS. 2A, 2B, and 2C show the aperture array in various configurations as used during testing. In the first configuration, shown in FIG. 2A and referred to as the 'one aperture' configuration, all apertures bar one are blocked off so that light can only pass through the single aperture. In the second configuration, show in FIG. 2B and referred to as the 'two aperture' configuration, all apertures bar two are blocked off. In this example, the two unblocked apertures are symmetrically disposed in the array with respect to a line passing horizontally through the aperture array. In the third configuration, show in FIG. 2B and referred to as the 'four aperture' configuration, all apertures bar four are blocked off. In this example, the four unblocked apertures are symmetrically disposed in the array with respect to a line passing horizontally through the aperture array.

Figure 3:
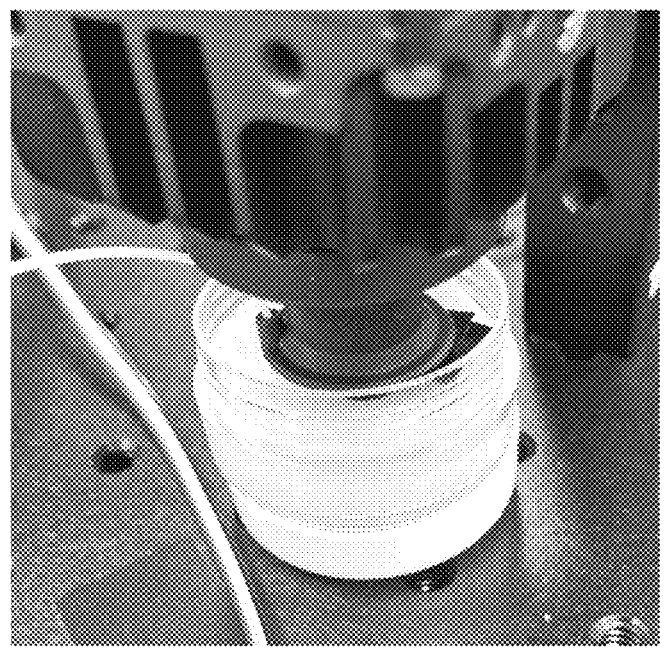
FIG. 3 shows an experimental setup used for testing the aperture array.

FIG. 3 shows an experimental setup used for testing the aperture array in each of the three configurations. A Keysight power supply was used to drive a Q-Photonics DFB laser with an operating wavelength 1300 nm and operating power of 10 mW. Data was acquired through a National Instruments DAQ. The optical receiver was an WiDy SEnS 640V-STEP gated mode camera, and the aperture array was connected to it such that light from the laser passed through a gelatine phantom and back through the aperture array to the camera. The camera's pixels had an active area of around 15 µm, and the apertures in the aperture array had a diameter of 1 mm. The camera sensor was positioned 2.5 cm from the gelatine phantom, and as discussed the operating wavelength of the laser was 1300 nm. The size of the speckles can therefore be calculated as:

$$((1300\times 10^{-9}\text{ m})\cdot(2.5\times 10^{-2}\text{ m}))/(1\times 10^{-3}\text{ m})=32.5\text{ µm}$$

The speckles therefore had a size which was approximately twice the active area of the pixels. A 7×7 sliding window was used to calculate speckle contrast (using the MATLAB function colfilt). The contrast, K, was calculated as $$K = \frac{\text{std of window}}{\text{mean of window}}.$$

The average speckle contrast was determined from the whole frame, and the average intensity was calculated by averaging the pixel intensities from the whole frame.

During the experiments, the camera mode was set to linear with gain set as high. For the one aperture configuration a 20 ms exposure time was used. For the two aperture configuration a 10 ms exposure time was used. For the four aperture configuration a 5 ms exposure time was used. The data was acquired as a 16-bit TIFF image via Snapshot.

Figure 4:
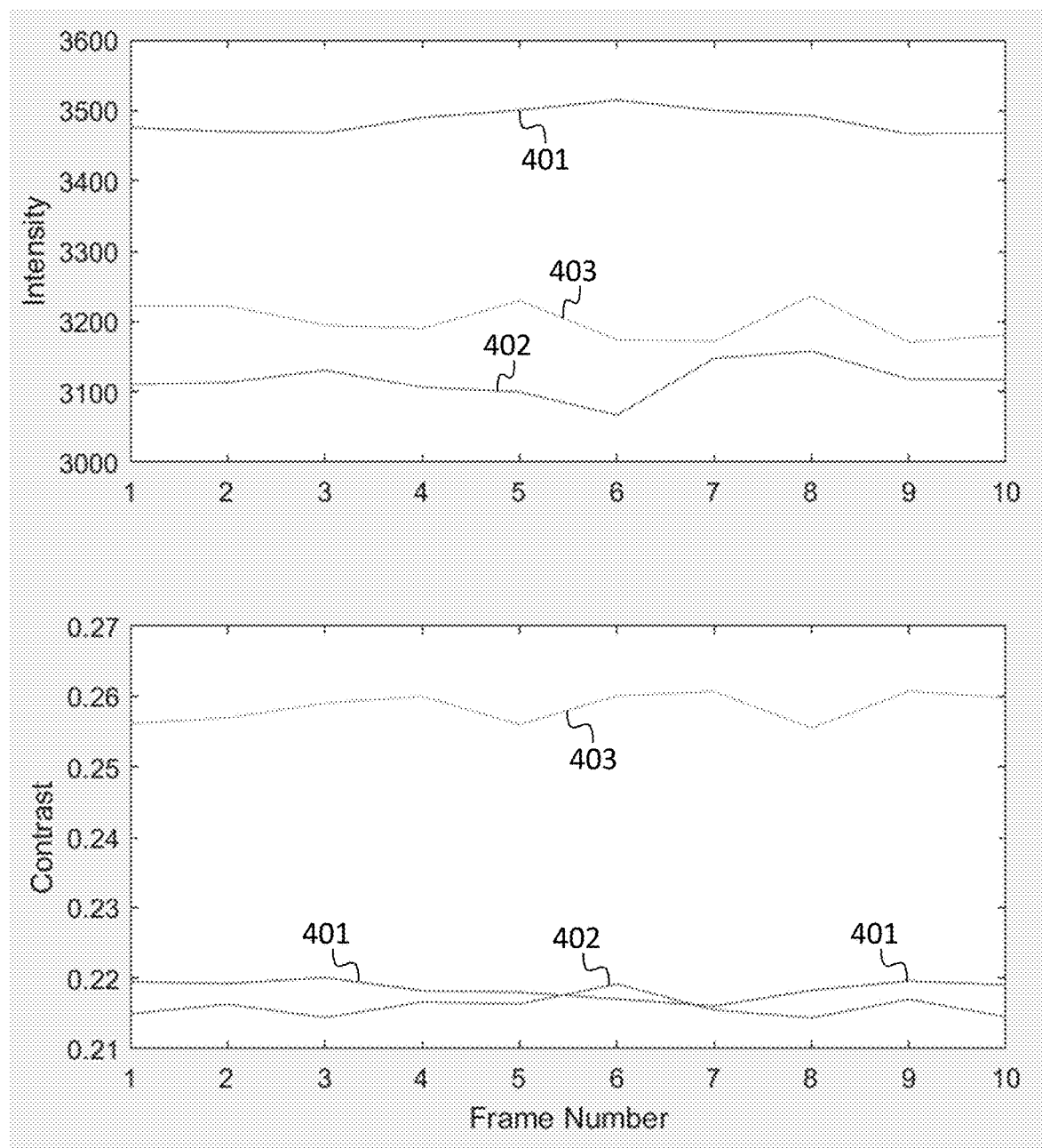
FIG. 4 shows plots of intensity (upper) and contrast (lower) against frame number for the one, two, and four aperture configurations.
Figure 5A:
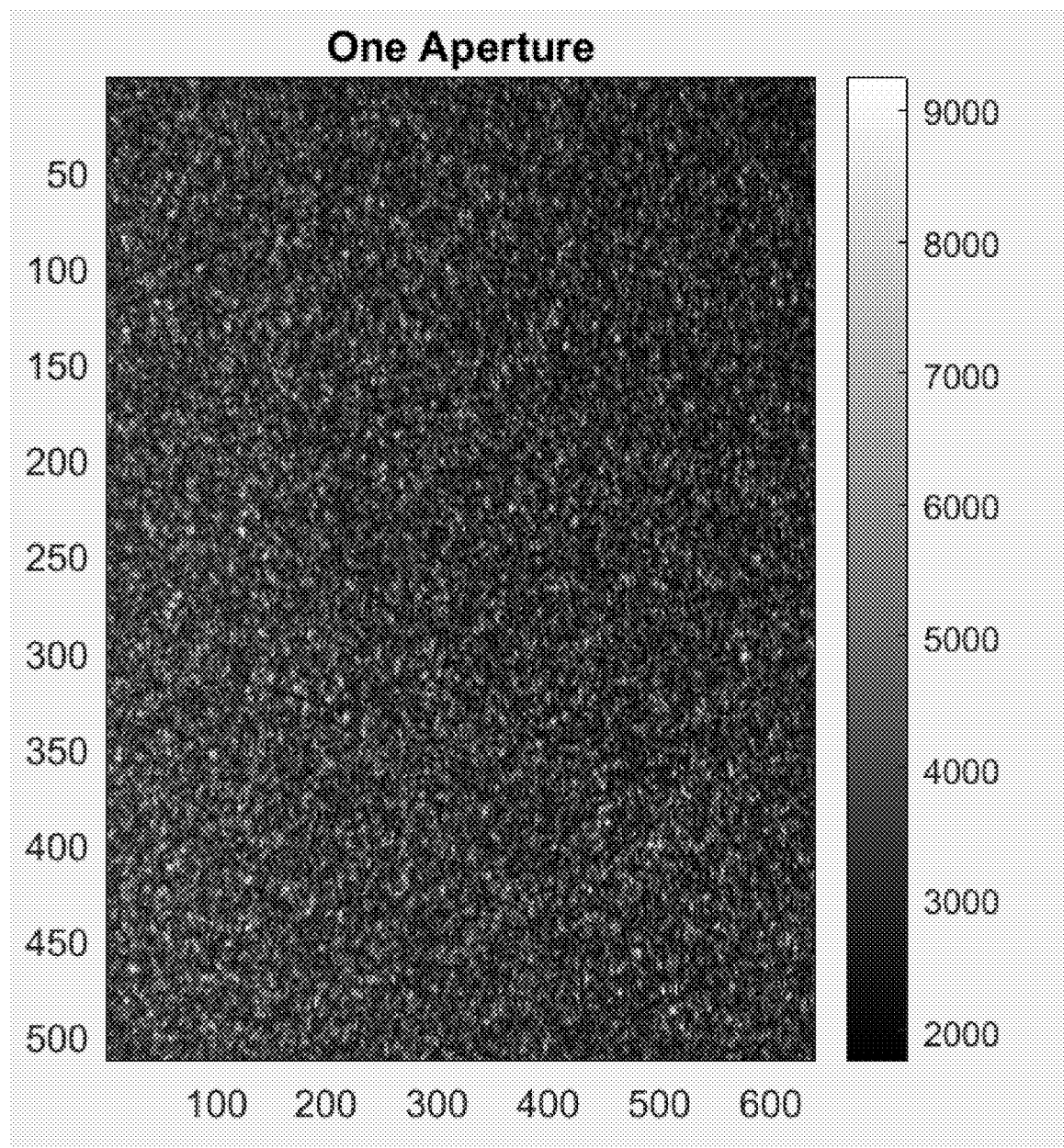
FIGS. 5A, 5B, and 5C show respective sample frames for each of the one, two, and four aperture configurations.
Figure 5B:
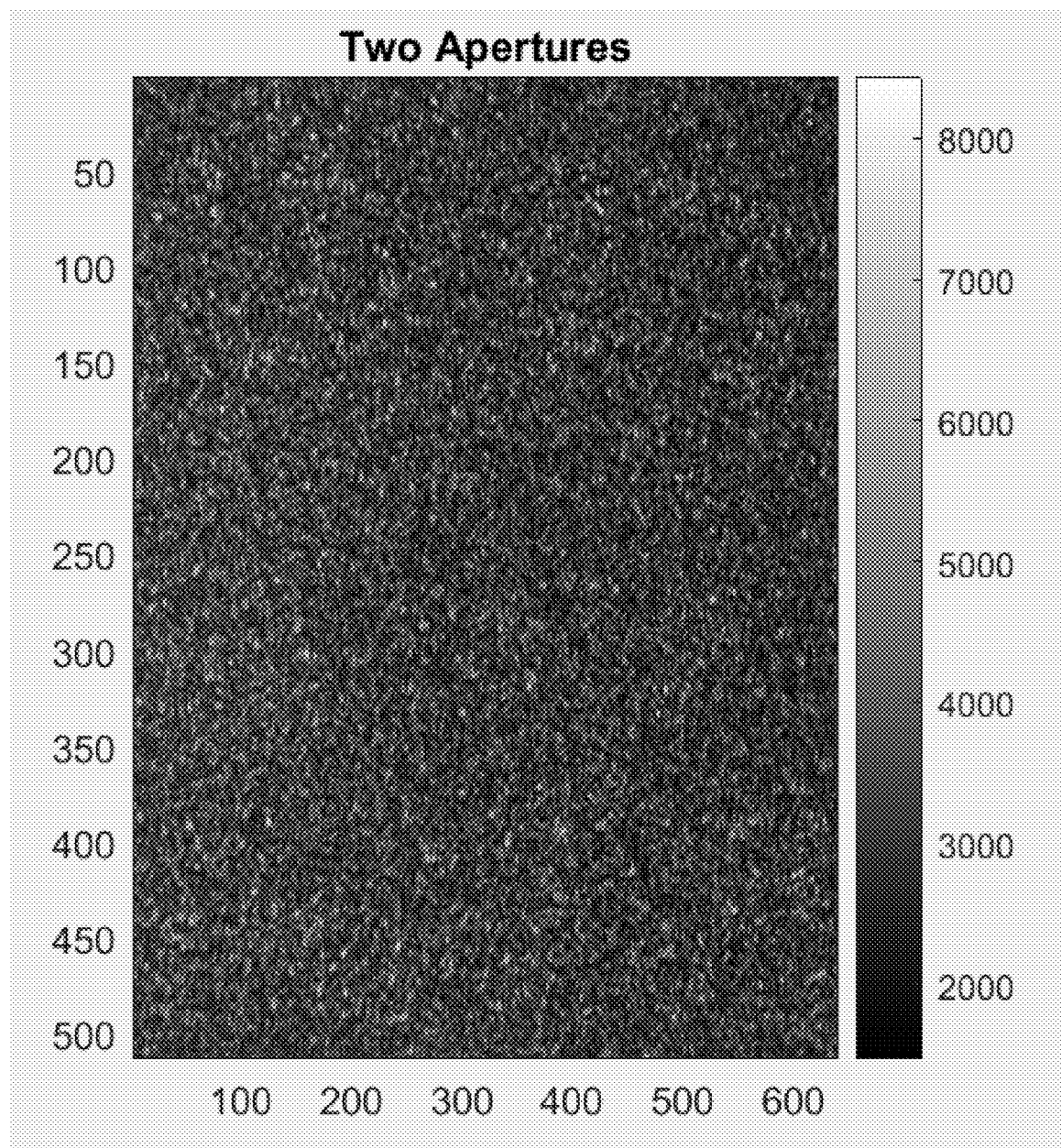
Figure 5C:
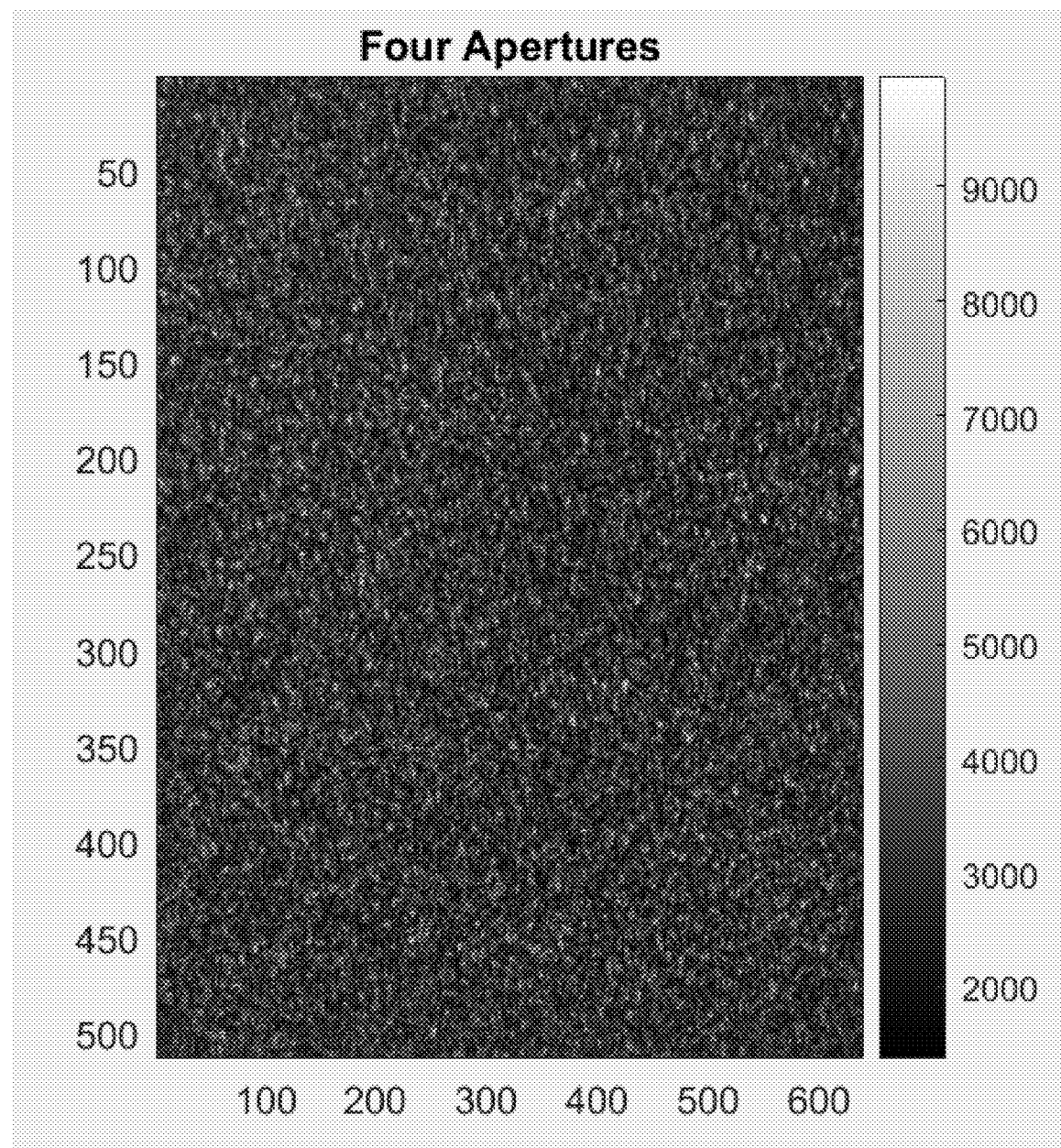

FIG. 4 shows plots of intensity (upper) and contrast (lower) against frame number for the one, two, and four aperture configurations (shown in a first curve 401, a second curve 402, and a third curve 403, respectively, in each of the two plots) as processed through the experimental setup discussed above. Of note is that the average intensity is similar for the different configurations with different exposure times, and increasing the number of apertures does not result in a reduction of contrast. Therefore, it can be understood that the aperture provides more light to the optical receiver and can also reduce the distance needed from the sample (e.g. skin) to the detector. FIGS. 5A, 5B, and 5C show respective sample frames for each of the one, two, and four aperture configurations.

A second experiment was then performed, using the same setup as discussed above but where the gelatine phantom had been replaced with a human finger. 200 images were acquired at 50 frames per second. To derive a spatial speckle contrast, a 7×7 sliding window was applied and then averaged for each image across all of the images. To derive a temporal speckle contrast, the standard deviation was divided by the mean of each pixel over the 200 images and then averaged. Table 1 below shows the results of this:

TABLE 1

| Sample | Apertures | Mean Intensity | Spatial SC ($K_S$) | Temporal SC ($K_t$) | CSD |
|---|---|---|---|---|---|
| Gelatine | 1 | 3201 | 0.2569 | 0.0732 | 0.4433 |
| Gelatine | 4 | 3230 | 0.2429 | 0.0561 | 0.3755 |
| Finger | 1 | 2002 | 0.1421 | 0.1477 | 1.0194 |
| Finger | 4 | 3167 | 0.1916 | 0.2004 | 1.0225 |

CSD is the coefficient of Speckle Dynamics, and is calculated using the equation $$CSD = \frac{2K_t}{K_S + K_t}.$$

The results in Table 1 suggest that the benefit of multiple apertures extend not only to enhancing the spatial speckle contrast, but also the temporal speckle contrast.

Figure 6A:
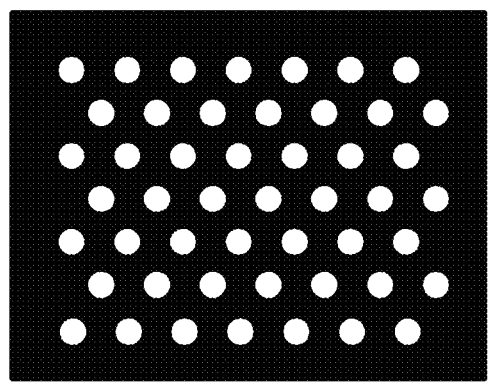
FIG. 6A shows a schematic setup of an aperture array, provided on a plate.
Figure 6B:
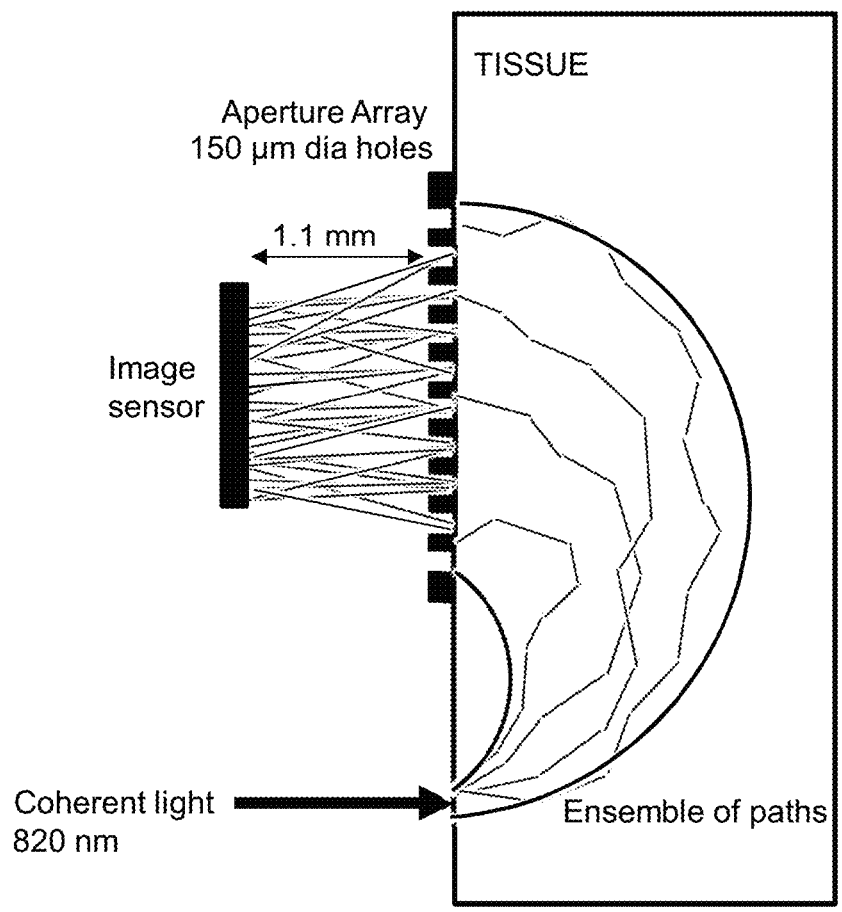
FIG. 6B shows how light passes through the system.

FIG. 6A shows a schematic setup of an optical transceiver using an optical speckle receiver with aperture array and FIG. 6B shows how light passes through the system. Coherent light with a wavelength of around 820 nm illuminates the tissue. The light traverses an ensemble of paths, creating speckle at the output of the tissue surface. An aperture plate comprised of 150 micron diameter holes collects light from different regions of the tissue. The aperture array here is provided as a plurality of holes (which are voids e.g. unfilled), or holes filled with a light-transmitting material) in a material, but could also be provided as an array of fibres (e.g. an array of fibre optic cables). The light from the aperture array mixes, creating a new speckle pattern on the image sensor, but with the same contrast as would arise from a single aperture. With this aperture size, the image sensor may be placed in close proximity to tissue, for example only 1.1 mm from the aperture plate. For such a system, the speckle size can be calculated using the equation $S=\lambda Z/D$, and using the values: $\lambda=820$ nm; $D=150$ µm; and $Z=1.1$ mm a speckle size of 6 µm can be obtained, which is sufficiently large for a sensor with 3 micron pixels.

Figure 7A:
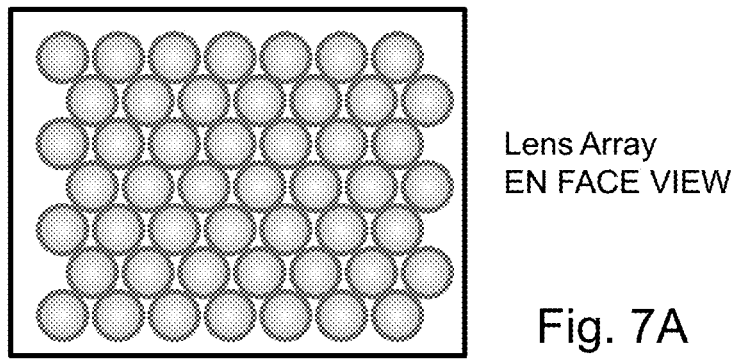
FIG. 7A shows a schematic setup of a lens array and FIG. 7B shows how light passes through the system.
Figure 7B:
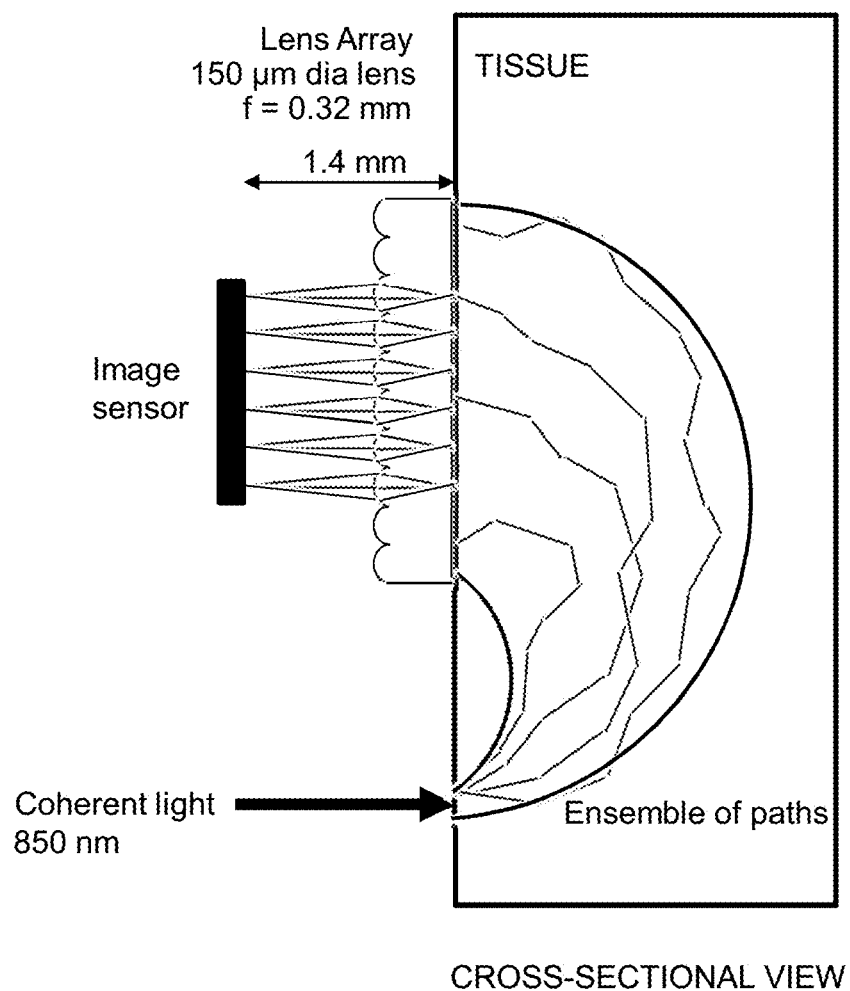

FIG. 7A shows a schematic setup of an optical transceiver using an optical speckle receiver with lens array and FIG. 7B shows how light passes through the system. In this example, a microlens array collects light from different regions of the tissue. The microlens array may be comprised of individual lenses (i.e. physically discrete) or be a monolithic block. The material surrounding the lenses may be clear or opaque to reduce background light. Each microlens has a diameter of 150 microns and a focal length of 0.32 mm. The substrate thickness is such that the distance to the tissue surface is effectively 0.5 mm. From the lens equation, the image is formed at 0.9 mm with magnification of 1.8. For such a system, the speckle size can be calculated using the equation S 1.2(1+M)$\lambda f_{\#}$ where $f_{\#}$ is the ratio between the lens focal distance and the effective aperture of the lens, and using the values: $\lambda=850$ nm; $f_{\#}=0.3$ mm/150 µm; M=1.8. The calculated speckle size is 6.1 microns, which is sufficiently large for a sensor with 3 micron pixels.

Figure 8:
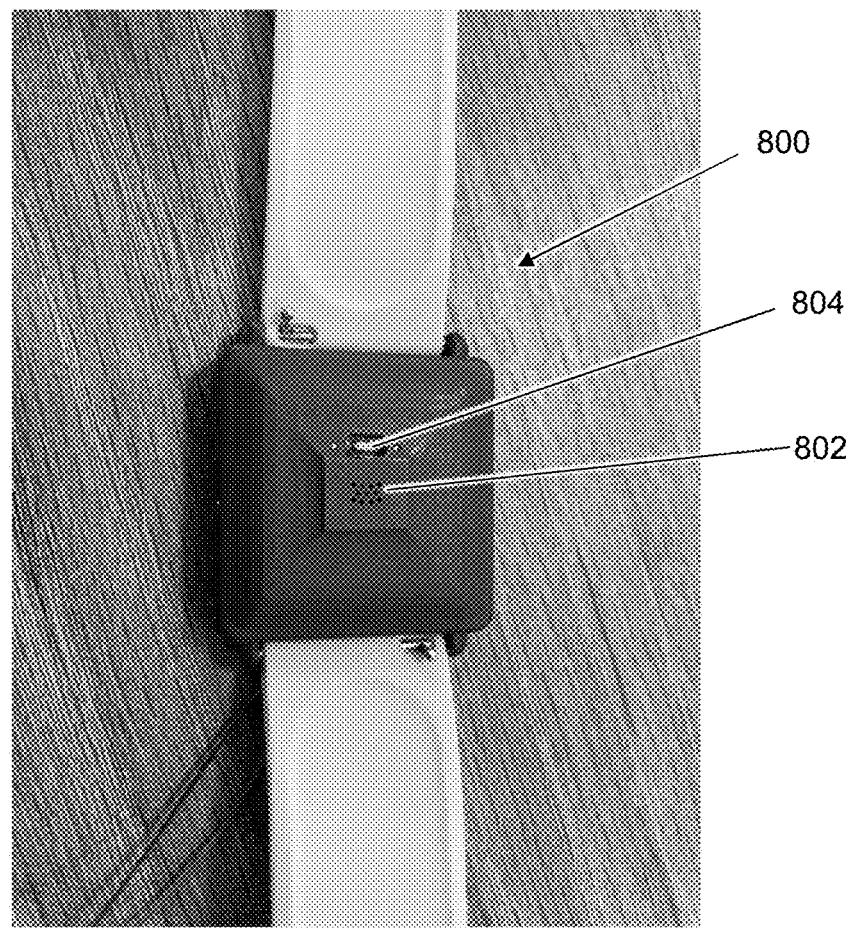
FIG. 8 shows a wearable device including an aperture array.

FIG. 8 shows a wearable device 800 including an aperture array 802. The aperture array is mounted on the rear of the wearable device, which in this example is a wristband including the main device housing and a wrist strap. In use, the aperture array will be pressed against the skin of the user with a gap between the coherent light source 804 and the skin of the user. That is, the aperture array 802 projects further from the wearable, in a direction towards the skin of the user, than the coherent light source 804.

Figure 9:
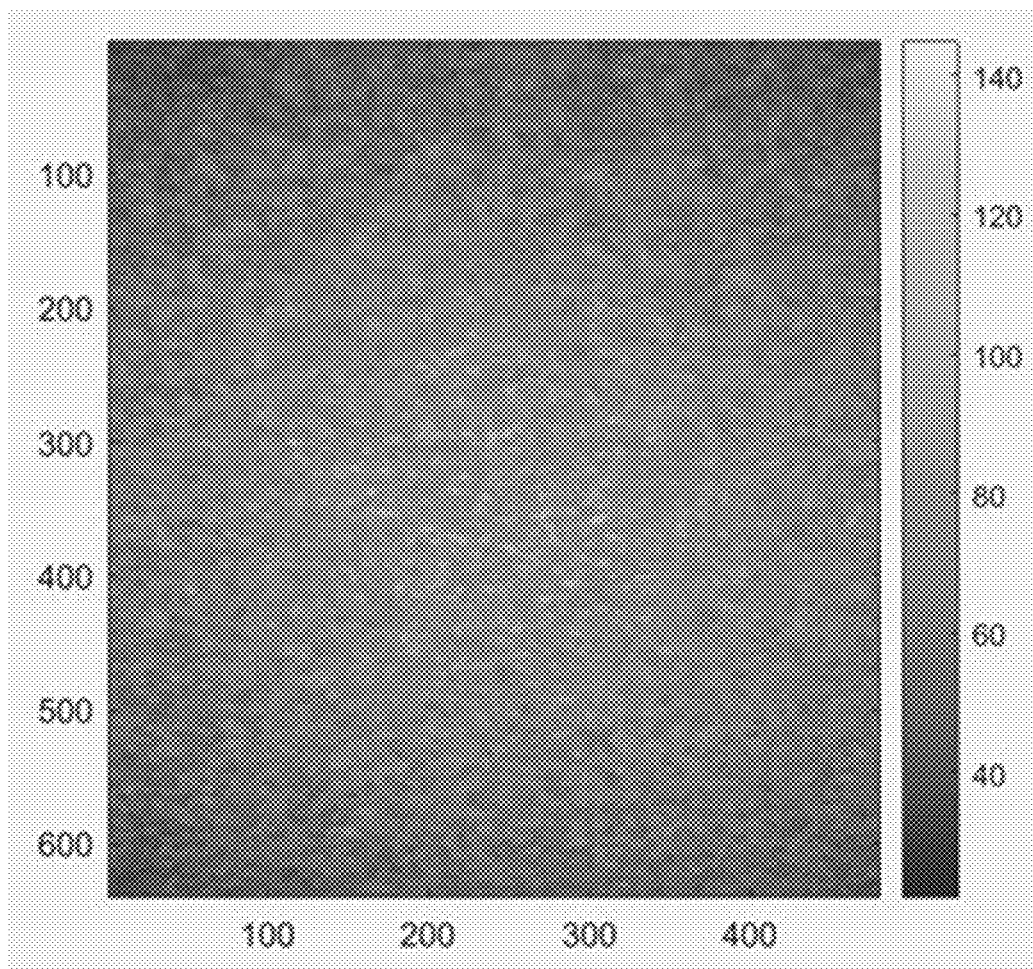
FIG. 9 shows a raw speckle image as acquired by the optical receiver through the aperture array.
Figure 10:
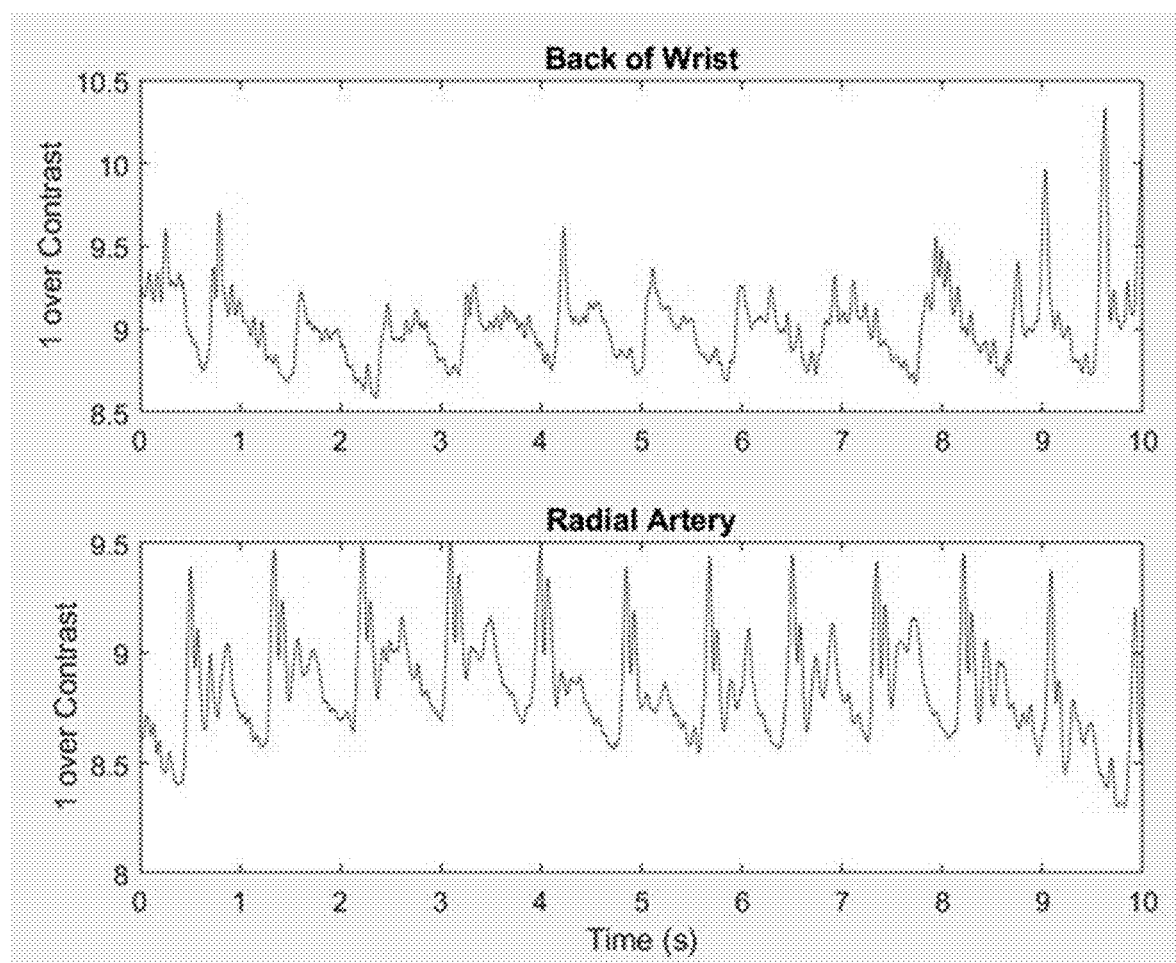
FIG. 10 shows plots of 1 over contrast against time where the optical receiver is located on the back of a person's wrist (upper) and over their radial artery (lower)

FIG. 9 shows a raw speckle image as acquired by the optical receiver through the aperture array. FIG. 10 shows plots of 1 over contrast against time where the optical receiver is located on the back of a person's wrist (upper) and over their radial artery (lower). The data for the plots was arrived at after processing the raw speckle image. As can be seen, pulsating components are visible which indicates the speckle image is suitable to derive the heart rate of the user.

Figure 11A:
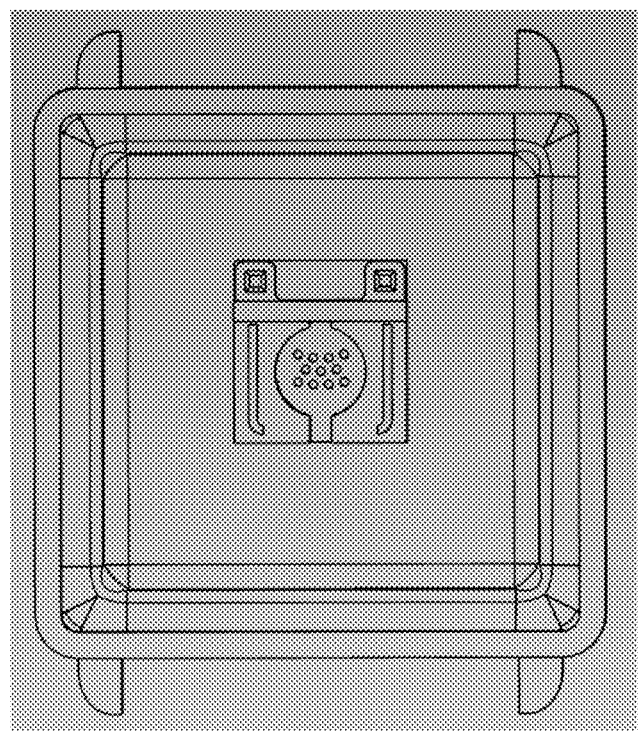
FIG. 11A-11C show CAD images for a wearable from a sensor top side, sensor bottom side, and sensor top side (angle) respectively.
Figure 11B:
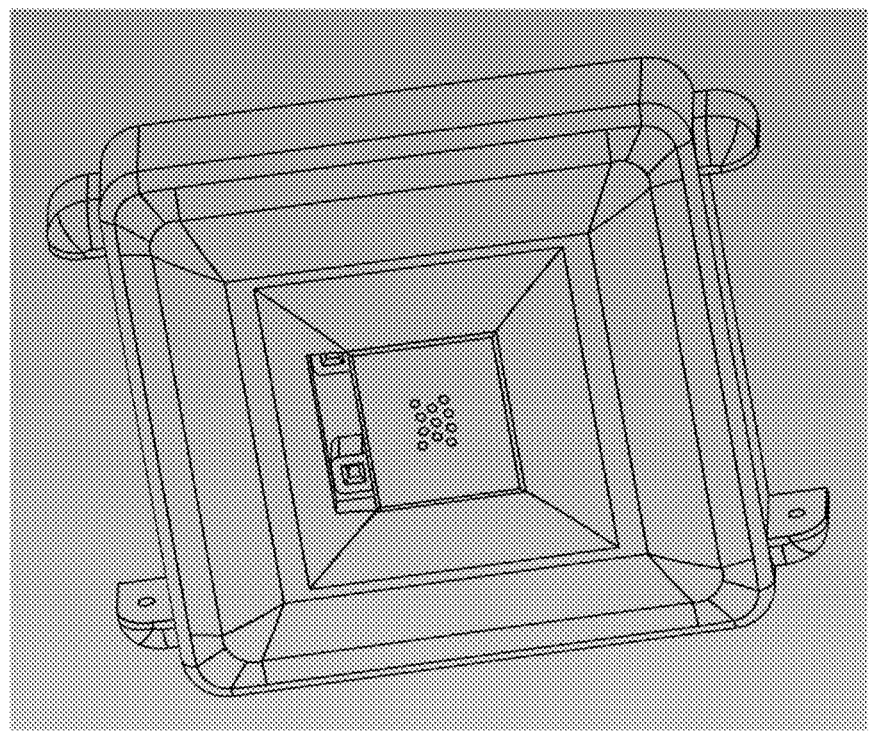
Figure 11C:
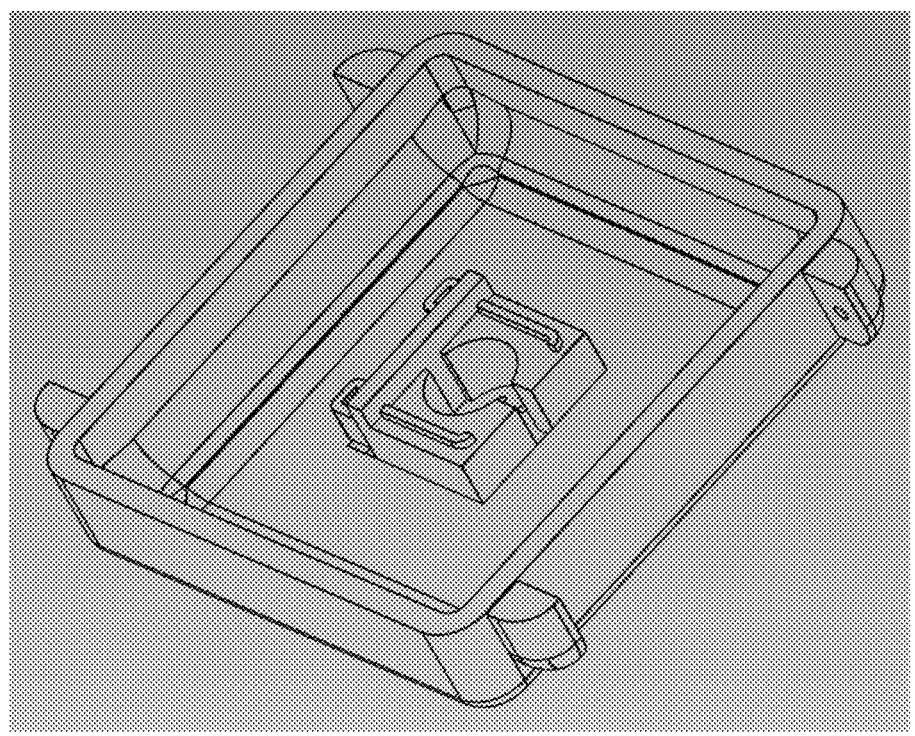

FIGS. 11A-11C show CAD images for a wearable from a sensor top side, sensor bottom side, and sensor top side (angle) respectively. The light source and/or apertures for the sensor may be designed to protrude so that they make better contact with the skin. Improved contact may enhance the speckle measurements by reducing specular reflectance.

Figure 12:
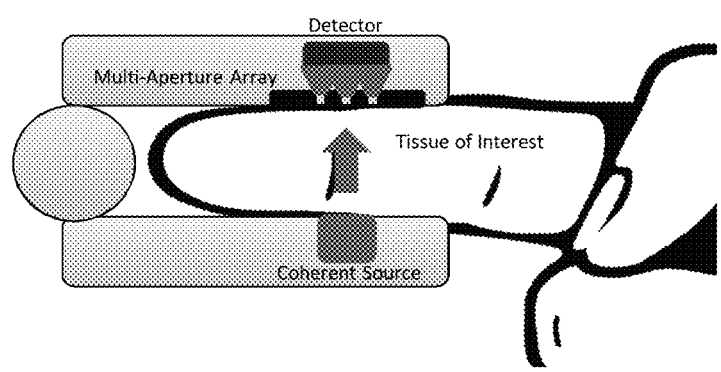
FIG. 12 shows an alternative arrangement for a wearable including an optical receiver and aperture array.
Figure 13:
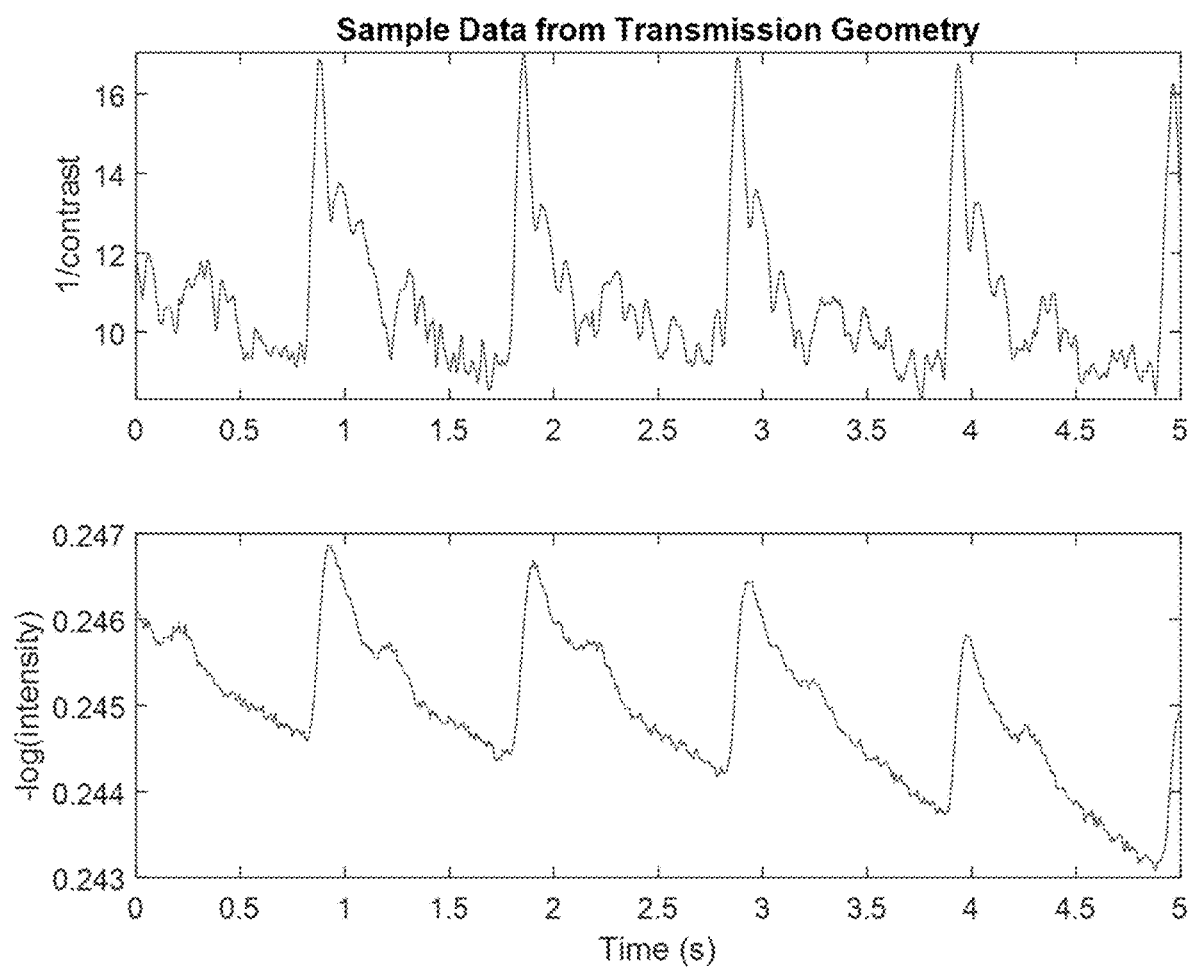
FIG. 13 shows a plot of 1/contrast (upper) and −log (intensity) (lower) against time for data collected from the arrangement in FIG. 12.

FIG. 12 shows an alternative arrangement for a wearable including an optical receiver and aperture array. This arrangement is referred to as a transmission arrangement or transmission mode (as opposed to the arrangement shown in FIGS. 6A and 6B which are reflection arrangements or reflection modes). For example, the wearable may be a ring or similar such that it at least partially encloses a portion of the user. In the transmission mode, the coherent light source is located across a testing region from the aperture array and detector. Tissue of interest, for example a patient's finger, is positioned in the testing region and so the coherent light passes through it to the multi-aperture array and on to the detector. In this example, the transmission arrangement is provided as a finger-clip type device where two generally planar elements are hingedly connected at one end to allow them to move towards and away from each other. The patient introduces their finger between the planar elements and spectrophotonic sampling is performed. FIG. 13 shows a plot of 1/contrast (upper) and −log(intensity) (lower) against time for data collected from the arrangement in FIG. 12. Again, as can be seen, pulsating components are visible which indicates the speckle image is suitable to derive the heart rate of the user.

Depending on the distance from the skin to the detector for speckle matching, increasing the number of holes or apertures in the aperture array may provide increased power as compared to the use of a single mode fiber. Further, as compared to a single mode fiber or waveguide, the aperture array disclosed herein may be more robust to dirt and hair. Additionally, the multi-aperture approach adopted in the aperture array can require less precise alignment between any given aperture and the optical receiver.

The features disclosed in the description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

All references referred to above are hereby incorporated by reference.

The invention claimed is:

1. An optical speckle receiver, comprising:
    an optical detector;
        a plurality of apertures, or
        a plurality of lenses; and
    a free propagation region between the optical detector and the apertures or the lenses,
    wherein each of the apertures or the lenses is configured to receive a respective speckle signal from a respective discrete location on a sample, and to transmit the respective speckle signal onto the optical detector through the free propagation region,
    wherein the free propagation region is configured such that respective speckle signals transmitted from at least two of the apertures or from at least two of the lenses spatially overlap on the optical detector.

2. The optical speckle receiver of claim 1, wherein the speckle receiver comprises the plurality of lenses.

3. The optical speckle receiver of claim 2, wherein the lenses are individual lenses.

4. The optical speckle receiver of claim 2, wherein the lenses are a monolithic block of lenses.

5. The optical speckle receiver of claim 2, wherein the lenses are exposed to an exterior of the optical speckle receiver.

6. The optical speckle receiver of claim 1, wherein the speckle receiver comprises the plurality of apertures, and wherein the apertures are holes in a plate.

7. The optical speckle receiver of claim 1, wherein the free propagation region defines an entire space between the optical detector and the lenses or apertures.

8. An optical speckle transceiver, comprising:
    the optical speckle receiver of claim 1; and
    a coherent light source configured to illuminate the apertures or lenses through the sample.

9. The optical speckle transceiver of claim 8, wherein the coherent light source and the apertures or lenses are configured to face opposite surfaces of the sample.

10. The optical speckle transceiver of claim 8, wherein the coherent light source and the apertures or lenses are configured to face a same surface of the sample.

11. A wearable device, comprising:
the optical speckle receiver of claim 1; and
a coherent light source configured to illuminate the apertures or lenses through the sample.

12. An optical speckle receiver comprising:
an optical detector; and
a plurality of holes in a plate, each hole corresponding to an aperture of an aperture array,
wherein each of the holes is configured to receive a respective speckle signal from a respective discrete location on a sample, and to transmit the respective speckle signal onto the optical detector.

13. The optical speckle receiver of claim 12, wherein the holes are voids in the plate.

14. The optical speckle receiver of claim 12, wherein the holes are filled with a light-transmitting material.

15. The optical speckle receiver of claim 12, wherein the plate is exposed to an exterior of the optical speckle receiver.

16. The optical speckle receiver of claim 12, wherein the optical detector is optically coupled with the holes such that at least two speckle signals respectively transmitted from at least two of the holes partially overlap on the optical detector.

17. An optical speckle transceiver, comprising:
an optical detector;
a plurality of apertures arranged in a plane, or
a plurality of lenses arranged in a plane; and
a coherent optical output comprising a window in an outer surface of the optical speckle transceiver, the window being offset from the apertures or the lenses along a direction perpendicular to the plane,
wherein each of the apertures or the lenses is configured to receive a respective speckle signal from a respective discrete location on a sample, and to transmit the respective speckle signal onto the optical detector.

18. The optical speckle transceiver of claim 17, wherein the coherent optical output is in a first portion of the optical speckle transceiver, and the apertures or lenses are in a second portion of the optical speckle transceiver protruding from the first portion.

19. The optical speckle transceiver of claim 17, wherein the apertures or lenses are in a first surface of the optical speckle transceiver, and the optical speckle transceiver is configured such that a gap is formed between the coherent optical output and the sample when the first surface is placed on the sample.

20. The optical speckle transceiver of claim 17, wherein the optical detector and the apertures or lenses face are configured to face a same surface of the sample.

* * * * *